(12) United States Patent
Yoon et al.

(10) Patent No.: US 10,959,619 B2
(45) Date of Patent: Mar. 30, 2021

(54) APPARATUS AND METHOD FOR ACQUIRING BIOLOGICAL INFORMATION AND BAND FOR ACQUIRING BIOLOGICAL INFORMATION

(71) Applicant: SAMSUNG ELECTRONICS CO., LTD., Suwon-si (KR)

(72) Inventors: Youngzoon Yoon, Hwaseong-si (KR); Hyungjoo Kim, Seongnam-si (KR); Younggeun Roh, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 550 days.

(21) Appl. No.: 15/450,303

(22) Filed: Mar. 6, 2017

(65) Prior Publication Data

US 2017/0251926 A1   Sep. 7, 2017

(30) Foreign Application Priority Data

Mar. 7, 2016   (KR) .................. 10-2016-0027148
Dec. 1, 2016   (KR) .................. 10-2016-0162910

(51) Int. Cl.
*A61B 5/00* (2006.01)
*A61B 5/02* (2006.01)
*A61B 5/021* (2006.01)

(52) U.S. Cl.
CPC ........ *A61B 5/0082* (2013.01); *A61B 5/02007* (2013.01); *A61B 5/02125* (2013.01);
(Continued)

(58) Field of Classification Search
CPC . A61B 5/0082; A61B 5/02125; A61B 5/7221; A61B 5/02007; A61B 5/6832; A61B 2562/04

See application file for complete search history.

(56) References Cited

U.S. PATENT DOCUMENTS

| 8,417,307 B2 | 4/2013 | Presura et al. |
| 9,554,724 B2 | 1/2017 | Schuessler |

(Continued)

FOREIGN PATENT DOCUMENTS

| JP | 2012-61232 A | 3/2012 |
| JP | 2013-103094 A | 5/2013 |

(Continued)

OTHER PUBLICATIONS

Masatsugu Niwayama et al.; "Error Factors in Oxygenation Measurement Using Continuous Wave and Spatially Resolved Near-infrared Spectroscopy"; The 17th Japanese Society for Medical Near-infrared Spectroscopy; The Journal of Japanese College of Angiology; vol. 52; Apr. 10, 2012; 5 pages total.

(Continued)

*Primary Examiner* — Jonathan Cwern
(74) *Attorney, Agent, or Firm* — Sughrue Mion, PLLC

(57) ABSTRACT

A biological information measuring apparatus, a method of acquiring biological information, and a biological information measuring band are provided. The biological information measuring apparatus may emit light beams in a direction, which is actively or passively adjusted, to a region of interest inside a target object, detect the light beams returning from the target object along trajectories different from one another, and select an optimum light beam among the detected light beams.

17 Claims, 13 Drawing Sheets

(52) U.S. Cl.
CPC .......... *A61B 5/6832* (2013.01); *A61B 5/7221* (2013.01); *A61B 2562/04* (2013.01)

(56) References Cited

U.S. PATENT DOCUMENTS

| | | | |
|---|---|---|---|
| 2004/0106856 A1* | 6/2004 | Kimura | A61B 5/0059 600/310 |
| 2007/0187632 A1* | 8/2007 | Igarashi | A61B 5/0048 250/559.36 |
| 2014/0316224 A1 | 10/2014 | Sato | |
| 2014/0343383 A1 | 11/2014 | Sato | |
| 2015/0062691 A1* | 3/2015 | Sayyah | H01Q 15/0086 359/316 |
| 2015/0313466 A1* | 11/2015 | Yoshida | A61B 5/0066 600/425 |
| 2016/0012749 A1* | 1/2016 | Connor | G09B 5/00 600/13 |
| 2016/0051169 A1* | 2/2016 | Hong | A63B 71/06 600/595 |
| 2016/0058300 A1 | 3/2016 | Yoon et al. | |
| 2016/0058374 A1* | 3/2016 | Matsuno | A61B 5/02438 600/324 |
| 2016/0106327 A1 | 4/2016 | Yoon et al. | |
| 2016/0113589 A1 | 4/2016 | Yoon | |
| 2016/0206251 A1 | 7/2016 | Kwon et al. | |
| 2016/0242647 A1 | 8/2016 | Ishii et al. | |
| 2016/0256116 A1 | 9/2016 | Baik et al. | |
| 2016/0278645 A1 | 9/2016 | Yoon | |

FOREIGN PATENT DOCUMENTS

| | | |
|---|---|---|
| JP | 2013-121420 A | 6/2013 |
| JP | 2015-92151 A | 5/2015 |
| KR | 10-2015-0068333 A | 6/2015 |
| KR | 10-2016-0115017 A | 10/2016 |

OTHER PUBLICATIONS

X. F. Teng et al.; "Continuous and Noninvasive Estimation of Arterial Blood Pressure Using a Photoplethysmographic Approach"; Proceedings of the 25th Annual International Conference of the IEEE EMBS; Sep. 17-21, 2003; 4 pages total.

Y. S. Yan et al.; "Noninvasive Estimation of Blood Pressure Using Photoplethysmographic Signals in the Period Domain"; Proceedings of the 2005 IEEE; Engineering in Medicine and Biology 27th Annual Conference; Sep. 1-4, 2005; 2 pages total.

Tim R. Dargaville et al.; "Sensors and imaging for wound healing: A review"; Biosensors and Bioelectronics; vol. 41; 2013; 13 pages total.

Peter Elter et al.; "Noninvasive and nonocclusive determination of blood pressure using laser Doppler flowmetry"; SPIE; 1999; 9 pages total.

* cited by examiner

APPARATUS AND METHOD FOR ACQUIRING BIOLOGICAL INFORMATION AND BAND FOR ACQUIRING BIOLOGICAL INFORMATION

CROSS-REFERENCE TO RELATED APPLICATION

This application claims priority from Korean Patent Application No. 10-2016-0027148, filed on Mar. 7, 2016, and Korean Patent Application No. 10-2016-0162910, filed on Dec. 1, 2016, in the Korean Intellectual Property Office, the disclosures of which are incorporated herein by reference in their entirety.

BACKGROUND

1. Field

Apparatuses and methods consistent with exemplary embodiments relate to an apparatus and a method for acquiring biological information, and more particularly, to an apparatus and a method for acquiring biological information regarding an inner area of a biological body based on a detected signal acquired by emitting a light beam to the biological body.

2. Description of the Related Art

Examples of methods for determining the mechanical characteristics of an inner area of a blood vessel of a living body include a method of detecting pulsation of an internal blood vessel based on a mechanical pressure by using a pressure sensor, a method of acquiring an incident wave and a reflected wave based on an optical mechanism, and a method using the characteristics of a biological body penetrable by ultrasound waves. The method utilizing a mechanical pressure sensor reduces a skin gap by applying a contact pressure in order to reduce signal reduction due to skin between a blood vessel and a sensor so that the pulse pressure information may be acquired while a skin influence is being reduced. According to this technique, which is referred to as Tonometry, continuous and stable application of pressure has a significant impact on the quality of a signal. The method using the permeation characteristics of ultrasound waves features deep permeation with minimized signal reduction due to a gel applied between an ultrasound wave emitting sensor and skin. However, miniaturization of a sensor to be used in this method is limited due to the necessity of using a gel and size limits of an ultrasound wave emitter and a detecting device. On the other hand, the method using transmittance and reflection of light enables fabrication of a sensor based on a combination of simple elements. However, the accuracy of the method using transmittance and reflection of light is quite low due to relatively poor permeation compared to ultrasound waves and variation of a skin gap between a blood vessel and skin from person to person.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide a biological information measuring apparatus, a method of acquiring biological information, and a biological information measuring band capable of accurately measuring biological information regarding structures of a blood vessel and skin that varies from person to person.

According to an aspect of an embodiment, there is provided a biological information measuring apparatus including: a light emitter configured to emit a plurality of light beams to a target object at incident angles different from one another; and a light detector configured to detect the plurality of light beams returning from the target object along trajectories different from one another based on the incident angles and acquire biological information of the target object based on at least one of the detected plurality of light beams.

The light emitter may include a light source configured to emit the plurality of light beams; and a light direction controller configured to adjust the incident angles of the plurality of light beams with respect to the target object.

The light direction controller may include a meta-material. The meta-material may include meta-atoms, and a distance between the meta-atoms may be changed according to a voltage applied to the meta-material.

The light emitter may include a plurality of light sources configured to emit the plurality of light beams in directions different from one another.

The plurality of light sources may be configured to emit light beams having a single wavelength or wavelengths different from one another.

The light emitter may include a light source configured to emit a light beam having multiple wavelengths; and a wavelength separating element configured to separate the light beam according to the multiple wavelengths.

Furthermore, the wavelength separating element may include at least one of a diffraction grating and a prism.

The light emitter may include at least two light sources that are disposed apart from each other, wherein the light detector is disposed between the at least two light sources, wherein a wavelength of light beams emitted from a first light source of the at least two light sources is different from a wavelength of light beams emitted from a second light source of the at least two light sources.

The light irradiator may include at least four light sources which are two-dimensionally arranged around the light detector and configured to emit the plurality of light beams having a single wavelength.

The light emitter may include a laser light source.

A partitioning wall may be disposed between the light emitter and the light detector.

According to an aspect of another embodiment, there is provided a method of acquiring biological information including: emitting a plurality of light beams to a target object at incident angles different from one another; detecting the plurality of light beams returning from the target object along trajectories different from one another based on the incident angles; and acquiring biological information of the target object based on at least one of the detected plurality of light beams.

The acquiring the biological information may include determining a light beam of the plurality of light beams as an optimum light in response to a correlation between the light beam and a reference light beam being greater than or equal to a predetermined value; and acquiring the biological information from the optimum light beam.

The emitting the plurality of light beams may include emitting at least two light beams along intersecting trajectories around the light detector.

The method may further include acquiring a blood flow velocity of the target object based on the at least one of the detected light beams by using the Doppler effect.

According to an aspect of another embodiment, there is provided a biological information measuring band including the above-stated biological information measuring apparatus and is configured to measure the biological information when the biological information measuring band is in contact with a skin of the target object.

The biological information measuring band may further include an attachment layer disposed on a skin contacting surface of the biological information measuring apparatus, the attachment layer including a protruding microstructure that is attachable to and detachable from the skin.

The biological information measuring band may further include a communication interface configured to wirelessly communicate with an external device; a controller configured to control the light emitter, the light detector, and the communication interface; and a battery configured to supply power.

The biological information measuring apparatus may be bendable.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
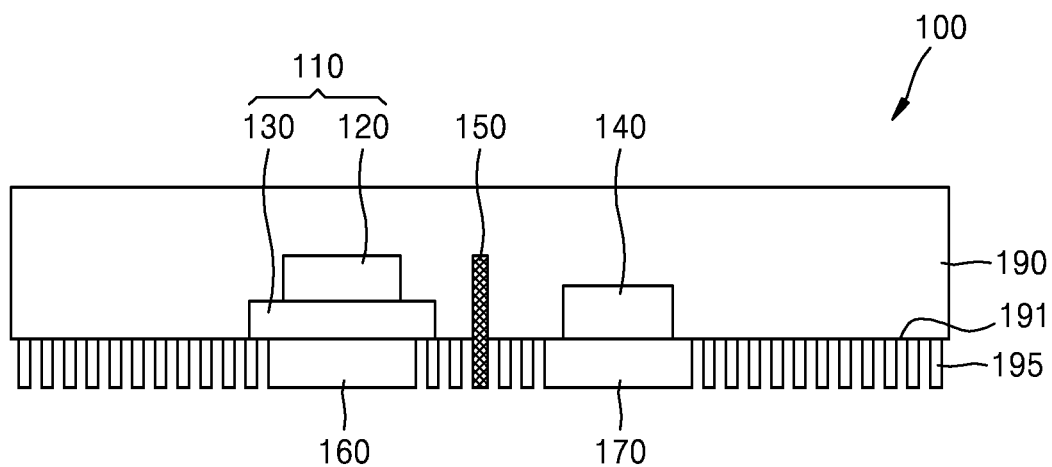
FIG. 1 is a schematic lateral sectional view showing a configuration of a biological information measuring apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail. As used herein, the term "and/or" includes any and all combinations of one or more of the associated listed items. Expressions such as "at least one of," when preceding a list of elements, modify the entire list of elements and do not modify the individual elements of the list.

It will be further understood that the terms "includes," "comprises," "including" and/or "comprising" used herein specify the presence of stated features or components, but do not preclude the presence or addition of one or more other features or components.

A biological information acquiring apparatus according to an exemplary embodiment may be a device that may be carried by a user, e.g., a wearable apparatus. The biological information acquiring apparatus may be any one of a wrist-watch type apparatus, a bracelet type apparatus, and a band type device apparatus having a communication function and a data processing function, or may include a combination of two or more thereof.

Figure 2:
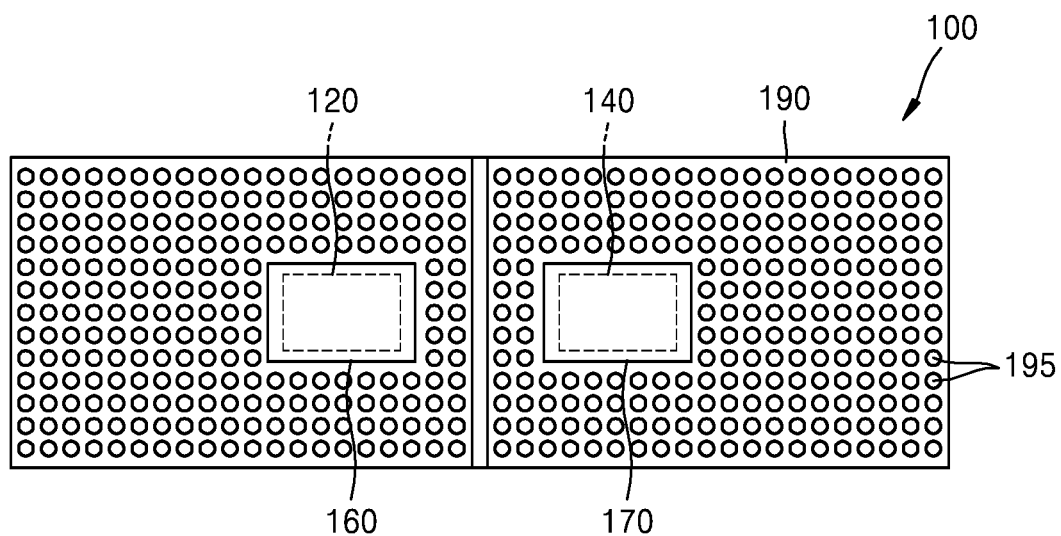
FIG. 2 is a bottom view of the biological information measuring apparatus of FIG. 1 according to an exemplary embodiment.

FIG. 1 is a schematic lateral sectional view showing a configuration of a biological information measuring apparatus 100 according to an exemplary embodiment, and FIG. 2 is a bottom view of the biological information measuring apparatus 100 of FIG. 1 according to an exemplary embodiment. For example, the biological information measuring apparatus 100 may be implemented with an optical spectrometer.

Referring to FIGS. 1 and 2, the biological information measuring apparatus 100 according to the present exemplary embodiment may include a light emitter 110 that emits a plurality of light beams to a target object at different incident angles and a light detector 140 that detects the plurality of light beams that are reflected, deflected, scattered or refracted from the target object after traveling in different trajectories according to the different incident angles. A light beam incident to a target object reacts with a material in the target object while traveling inside the target object, thereby acquiring the biological information. In other words, as a light beam is reflected, absorbed, and scattered based on the unique characteristics of a material in a target object, the light beam traveling in the target object acquires unique biological information. Since materials in a target object may differ according to their locations, light beams travelling along different trajectories may acquire different biological information.

The light emitter 110 may include a light source 120 that emits a light beam and a light direction controller 130 that controls a traveling direction of the light beam according to an electrical signal, such that the light beam is incident to a target object at a particular incident angle.

The light source 120 may be a laser light source, but is not limited thereto. The laser light source may include, for example, a semiconductor laser diode. According to some exemplary embodiments, the light source 120 may include a short-wavelength light emitting diode (LED).

A light beam emitted by the light source 120 may differ based on the types of materials of interest in a target object. For example, when a target object is a person and a material of interest is a material inside the skin of the target object, the light source 120 may emit a light beam having a wavelength in the red color range or the near-infrared ray range. The wavelength range described above is merely an example, and the light source 120 may emit a light beam having a different wavelength based on a material of interest.

The target object may be a person or an animal, but is not limited thereto. The target object may be a part in the target object. Furthermore, a material of interest in the target object and may be a material having inherent optical properties. A material of interest may be a biomaterial or a material including a combination of a biomaterial with a phosphor. For example, a material of interest may be a red blood cell, glucose, and high sensitivity C-reactive protein (hsCRP), where types of materials of interest are not limited.

Materials of interest may differ in absorption, transmission, and reflection of a light beam based on molecular bonding structures, molecular shapes, potential energy surfaces (PES), masses of atoms, vibration couplings, etc. Therefore, information regarding a material of interest, that is, biological information, may be acquired by figuring out characteristics of a light beam reflected or transmitted by the material of interest. A light beam with optical characteristics changed due to a reaction with a material of interest may be referred to as a light beam including biological information.

The light direction controller 130 may be disposed on a light emitting surface side of the light source 120. In some cases, an optical element for converting an optical path, such as a mirror or a total reflection prism, may be disposed between the light source 120 and the light direction controller 130.

The light direction controller 130 may control a direction of a light beam emitted by the light source 120. The light direction controller 130 may control either a reflection angle of a light beam reflected by the light direction controller 130 or a refraction angle at which a light beam passes through the light direction controller 130, according to an electrical signal. In other words, the direction of the light beam emitted by the light source 120 may be selectively changed by the light direction controller 130 so that the light beam enters the target object at a certain incident angle. The detailed structure of the light direction controller 130 will be described below.

The light detector 140 detects light beams having different trajectories in a target object. The light detector 140 may include a depletion layer photo diode, an avalanche photo diode, a photomultiplier tube, etc. Alternatively, the light detector 140 may be implemented as a complementary metal-oxide semiconductor (CMOS) image sensor or a charge-coupled device (CCD) image sensor. The light detector 140 may include a plurality of unit detection units, and each unit detection unit may further include an optical filter corresponding to a certain wavelength.

The biological information measuring apparatus 100 may further include a partitioning wall 150 disposed between the light emitter 110 and the light detector 140. The partitioning wall 150 may include a material capable of blocking light. The partitioning wall 150 blocks a light beam traveling toward the light detector 140 directly from the light emitter 110 without passing through a target object.

The light source 120, the light direction controller 130, the partitioning wall 150 and the light detector 140 may be mounted in a housing 190. The housing 190 may include a flexible material to be adapted to the curvature of an outer surface of a target object. In some cases, the housing 190 may have a shape that may be attached to a portion where biological information of a target object may be acquired. For example, when the housing 190 is attached to a wrist, the skin contacting surface 191 of the housing 190 may be disposed to conform to the shape of the wrist. In this case, the housing 190 may include a hard material.

The skin contacting surface 191 of the housing 190 may be disposed on an attachment layer 195 having a protruding microstructure. The attachment layer 195 may have a shape simulating a bio-adhesive structure, such as a gecko. The attachment layer 195 may easily attach the biological information measuring apparatus 100 to the skin of a target object (e.g., a person) and may be detached after the use. In another example, the skin contacting surface 191 of the housing 190 may be disposed with an adhesive layer including an adhesive, such as acrylic adhesive or silicon adhesive.

The housing 190 may further include first and second covers 160 and 170 that cover the light emitter 110 and the light detector 140, respectively. Each of the first and second covers 160 and 170 may protect the light emitter 110 and the light detector 140 from the outside. Furthermore, the first and second covers 160 and 170 may include a material with a high light transmittance in order to minimize loss of a light beam passing through the first and second covers 160 and 170. The first and second covers 160 and 170 may include a same material or different materials. Each of the first and second covers 160 and 170 may be disposed to overlap with the light emitter 110 and the light detector 140 along a light beam traveling direction.

Figure 3:
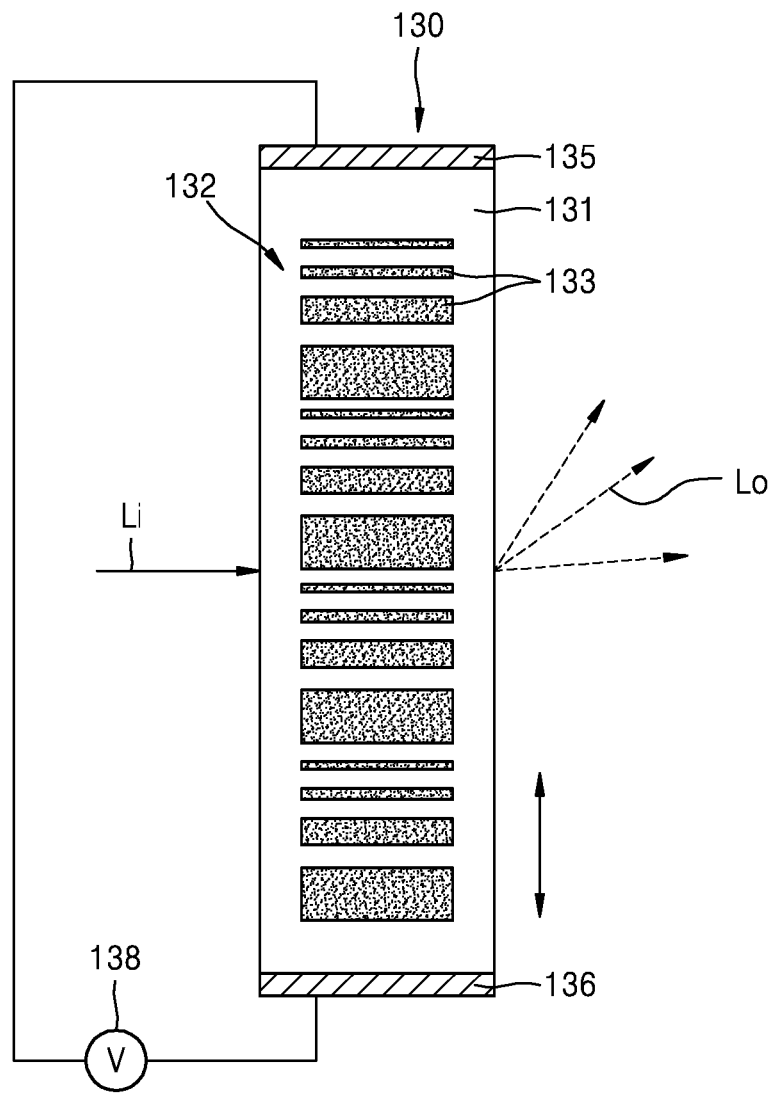
FIG. 3 is a diagram showing a specific configuration of a light direction controller in the biological information measuring apparatus of FIG. 1 according to an exemplary embodiment.
Figure 4:
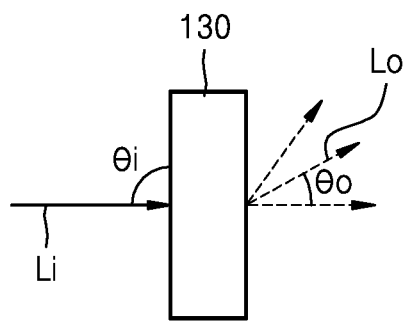
FIG. 4 is a diagram showing the operation of the light direction controller of FIG. 3 according to an exemplary embodiment.

FIG. 3 is a diagram showing a specific configuration of the light direction controller 130 in the biological information measuring apparatus 100 of FIG. 1, and FIG. 4 is a diagram showing the operation of the light direction controller 130 of FIG. 3.

For example, the light direction controller 130 may include an optical element in which a meta-material 132 capable of changing a travel path of a light beam is disposed. The meta-material 132 may have a structure in which a plurality of meta-atoms 133 are arranged in a fine pattern shape. Based on shapes, sizes, and arrangements of the meta-atoms 133 (e.g., a periodic arrangement or a quasi-periodic arrangement) of the meta-atoms 133, the meta-material 132 may have various effective properties. The meta-material 132 may be disposed on a surface of a piezoelectric body 131. The piezoelectric body 131 includes first and second electrodes 135 and 136. For example, the piezoelectric body 131 may have a rectangular shape, and the first and second electrodes 135 and 136 may be disposed on both side sides of the piezoelectric body 131. For example, as electric signals are applied to the first and second electrodes 135 and 136 by the power supply 138, the piezoelectric body 131 contracts or expands due to the piezoelectric phenomenon. The internal structure of the meta-material 132 (e.g., a distance between of the meta-atoms 133, size and shape of the meta-atoms 133, etc.) may be changed due to the contraction or expansion of the piezoelectric body 131.

The light direction controller 130 according to the present exemplary embodiment may refract or reflect an incident light beam at a certain angle by using the meta-material 132. For example, when the meta-material 132 has a transmissive structure, the light direction controller 130 may refract the incident light beam at a certain angle. When the meta-material 132 has a reflective structure, the light direction controller 130 may reflect the incident light beam at a certain angle. Furthermore, an angle of refraction or an angle of reflection may be changed according to voltages applied to the first and second electrodes 135 and 136.

Optical deflectivity may be adjusted based on the structure of the meta-atom 133, and also a distance between the meta-atoms 133. The distance between the meta-atoms 133 may be adjusted by using an electro-mechanical deformation phenomenon, such as a piezo phenomenon of a piezoelectric body.

Figure 5:
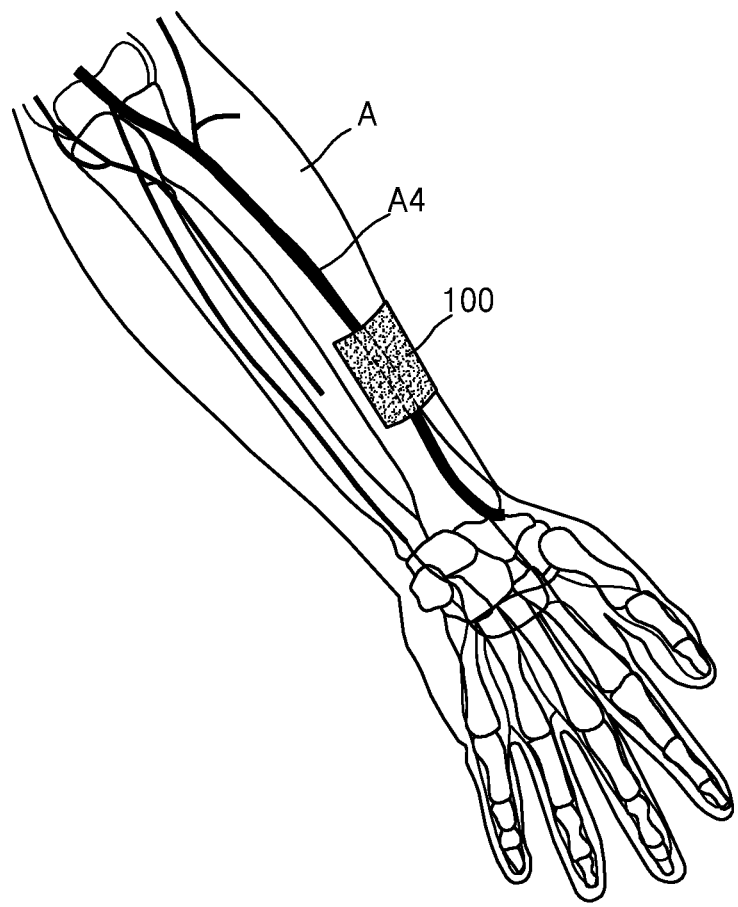
FIG. 5 is a diagram showing an example of using the biological information measuring apparatus of FIG. 1 according to an exemplary embodiment.

FIG. 5 is a diagram showing an example of using the biological information measuring apparatus 100 of FIG. 1. As shown in FIG. 5, the biological information measuring apparatus 100 according to an exemplary embodiment may include a band attached to the skin of a target object (e.g., person) A. By providing an attachment layer 195 or an adhesive layer on skin contacting surface 191 of the housing 190 as described above, the biological information measuring apparatus 100 may be stably and closely attached to the skin of the target object A. The biological information measuring apparatus 100 may be used to acquire internal biological information regarding the target object (e.g., a velocity of blood flow in a blood vessel A4).

Figure 6:
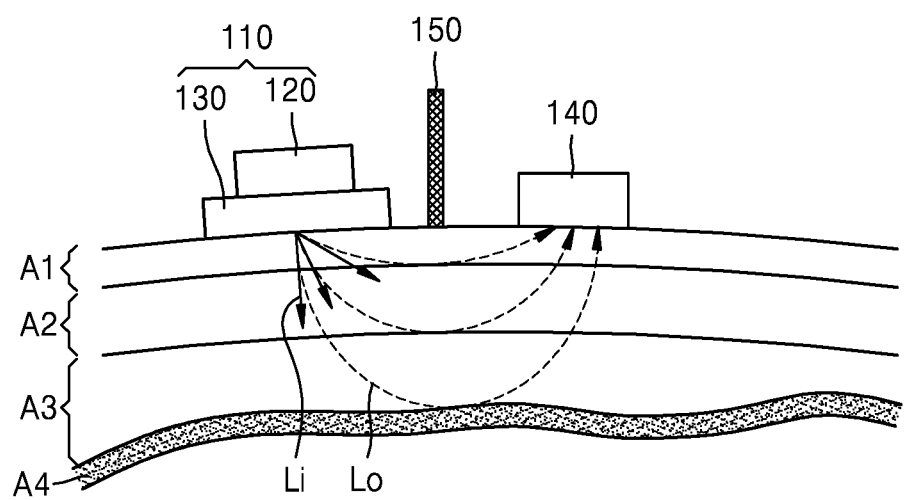
FIG. 6 is a diagram for describing the operation of the biological information measuring apparatus of FIG. 1 according to an exemplary embodiment.
Figure 7:
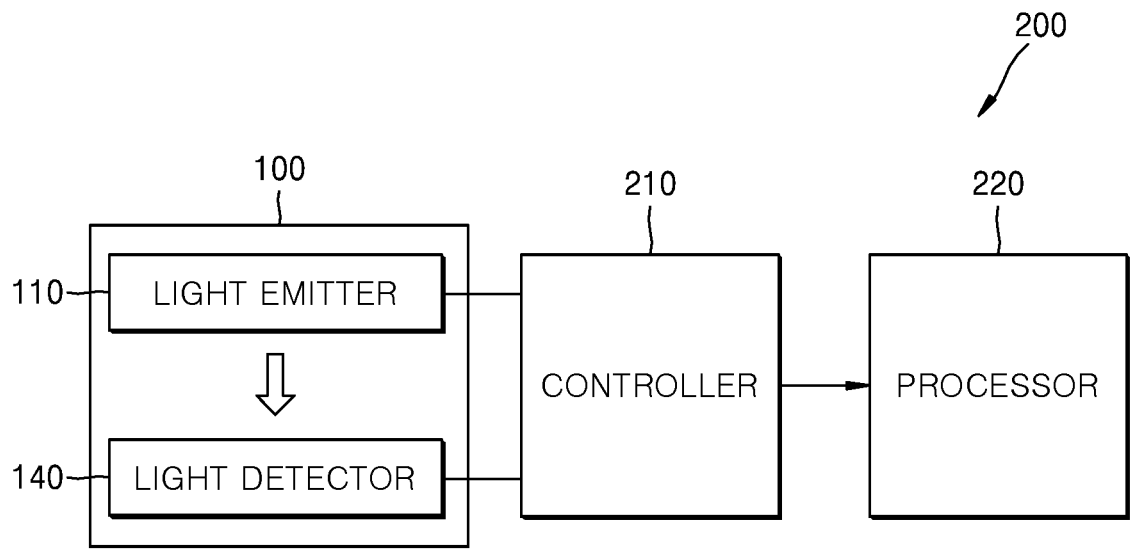
FIG. 7 is a block diagram of a biological information acquiring apparatus including the biological information measuring apparatus of FIG. 1 according to an exemplary embodiment.
Figure 8:
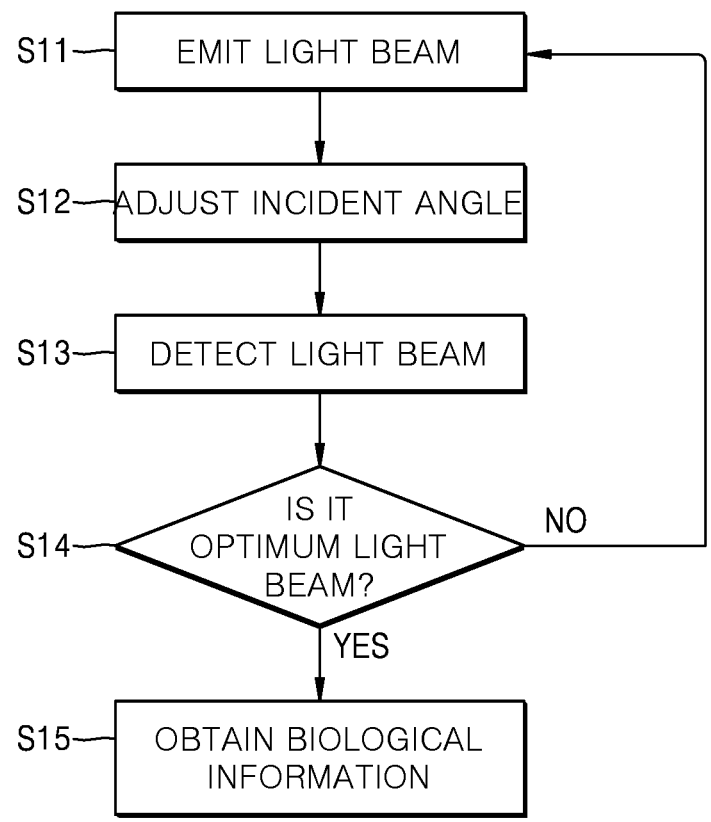
FIG. 8 is a flowchart of a method of acquiring biological information by using the biological information acquiring apparatus of FIG. 7 according to an exemplary embodiment.

FIG. 6 is a diagram for describing the operation of the biological information measuring apparatus 100 of FIG. 1, FIG. 7 is a block diagram of a biological information acquiring apparatus 200 including the biological information measuring apparatus 100 of FIG. 1, and FIG. 8 is a flowchart of a method of acquiring biological information by using the biological information acquiring apparatus 200 of FIG. 7.

Referring to FIGS. 6 through 8, the biological information acquiring apparatus 200 according to an exemplary embodiment includes the light emitter 110 that emits a plurality of light beams at different incident angles to a target object, such that the plurality of light beams have a plurality of trajectories different from one another, a controller 210 that determines at least one of the plurality of light beams corresponding to the plurality of trajectories as an optimum light beam, and a processor 220 that acquires biological information regarding the target object from the optimum light beam. The controller 210 may provide a signal (e.g., an electrical signal) to the light emitter 110 to control an incident angle of a light beam.

Here, the biological information measuring apparatus 100 may include the light emitter 110 and the light detector 140 to obtain a light beam including biological information. The biological information acquiring apparatus 200 may acquire biological information regarding a target object using a detected light beam and may include the processor 220.

The biological information acquiring apparatus 200 may be a single hardware apparatus including the biological information measuring apparatus 100, but is not limited thereto. For example, the processor 220 may be implemented in a separate apparatus from an apparatus including the light emitter 110 and the light detector 140. In FIG. 7, the controller 210 is shown as a component of the biological information acquiring apparatus 200, but is not limited thereto. The controller 210 may be a component of the biological information measuring apparatus 100, and the function of the controller 210 may be divided and some of the divided functions may be included in the biological information measuring apparatus 100.

The method of acquiring biological information using the biological information acquiring apparatus 200 includes operation S11 in which light beams are emitted from the light source 120 to a target object, operation S11 in which incident angles of the light beams are adjusted such that the light beams respectively have a plurality of trajectories different from one another, operation S13 in which the light beams returning after the target object is detected by the light detector 140; and operation S14 in which at least one of the light beams respectively corresponding to the plurality of trajectories different from one another in the target object is determined as an optimum light beam. Furthermore, the method may further include operation in which biological information is acquired from the optimum light beam. Since absorption, scattering, and reflection of a light beam differ based on characteristics of a material of interest, the processor 220 may acquire biological information regarding the target object based on a degree of change between characteristics of the incident light beam and characteristics of the detected light beam. Since the method of acquiring biological information according to optical characteristics is known in the art, detailed description thereof will be omitted.

In operation S12 for adjusting the incident angle, incident angles of light beams may be sequentially changed by using the light direction controller 130. For example, the light direction controller 130 may control a light beam to be incident to a target object at a first incident angle at a first time. In operation S13 for detecting a light beam, a light beam that acquired biological information by traveling inside the target object and reacting with a material in the target object may be detected.

In operation S13 for determining whether or not a light beam is an optimum light beam, it may be determined whether a detected light beam is an optimum light beam by using a correlation between the detected light beam and a reference light beam. Here, the reference light beam is light beam that becomes a reference when a light beam is detected by reacting with a material of interest and may be determined based on big data. A target object includes materials other than a material of interest. For example, velocity of red blood cells is measured in order to measure velocity of blood flow, but a light beam may be reflected by a blood vessel according to a path in which the light beam travels. At this time, information regarding a light beam reflected by red blood cells may be acquired based on various data from previously experiments, where the data may be referred to as information regarding a reference light beam. The information regarding the reference light beam may be stored in advance or may be updated based on acquired biological information.

When a correlation between detected light beam and the reference light beam is equal to or greater than a reference value, the controller 210 may determine the detected light beam as the optimum light beam. However, when the correlation is less than the reference value, the controller 210 may determine that the light beam is not an optimum light beam and may control the light emitter 110 to adjust the incident angle. Here, the reference value may also be set in advance.

When an optimum light beam is determined by repeating operations S11 to S14, the processor 220 may acquire biological information from the optimum light beam in operation S15. In operations S11 to S14, a light beam is emitted and detected one at a time and it is determined whether the light beam is an optimum light beam, but the present disclosure is not limited thereto. The light emitter 110 may sequentially emit a plurality of light beams, and the light detector 140 may sequentially detect a plurality of light beams. Next, the detected light beams may be respectively compared to a reference light beam to determine an optimum light beam.

Figure 9:
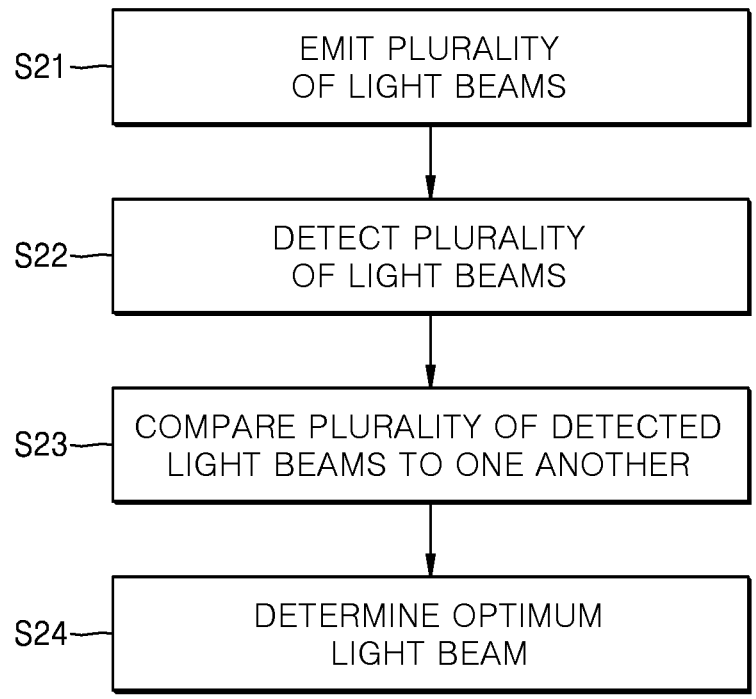
FIG. 9 is a flowchart of another method of acquiring biological information according to an exemplary embodiment.

FIG. 9 is a flowchart of another method of acquiring biological information.

The biological information acquiring apparatus 200 according to an exemplary embodiment may emit light beams to a target object while changing incident angles of the light beams, such that the emitted light beams have a plurality of trajectories different from one another in operation S21.

Next, the light detector 140 may detect a light beam that acquires biological information by reacting with a material in the target object from among the light beams travel in different trajectories within the target object in operation S22.

The controller 210 may compare the plurality of detected light beams in operation S23 to one another and determine an optimum light beam among the plurality of light beams in operation S24. Even when the light beams travel in different trajectories in the target object, the light beams may acquire biological information regarding a same material of interest. In other words, correlations with respect to a reference light beam may be within a permissible error range. In this case, the controller 210 may compare the plurality of detected light beams to one another and determine one of the light beams as an optimum light beam. For example, a light beam having the highest intensity may be determined as an optimum light beam.

The light emitter 110 may cause light beams having a plurality of wavelengths to be simultaneously incident on a target object. From among the light beams having a plurality of wavelengths, light beams having relatively short wavelengths are less transmissive with respect to the target object, whereas light beams having relatively long wavelengths are more transmissive with respect to the target object. Therefore, when the light beams having the plurality of wavelengths are incident into the target object, light beams having relatively short wavelengths pass through the target object via short trajectories, whereas light beams having relatively long wavelengths pass through the target object via long trajectories. Next, the light detector 140 may detect a light beam for respective wavelengths. Therefore, the controller 210 may determine at least one of the light beams detected for respective wavelengths as an optimum light. For example, a light beam, which is determined as a light beam reacted with a material of interest from among the light beams detected by being compared to a reference light beam, may be determined as an optimum light.

When the light direction controller 130 is applied to the light beams having a plurality of wavelengths, incident angles of the light beams may be adjusted for respective wavelengths. When the light source 120 emits light beams having a plurality of wavelengths, incident angles of the light beams may be adjusted either by using the light direction controller 130, which is an active element shown in FIG. 3, or by using a passive element. For example, the light direction controller 130 may include a wavelength separating element for separating a light beam having a multi-wavelength passing through the wavelength separating element from one another according to wavelengths. The wavelength separating element may be a diffraction grating or a prism. Light beams separated by the wavelength separating element may be incident to a target object at incident angles different from one another.

The biological information acquiring apparatus 200 according to an exemplary embodiment may also be used to acquire biological information regarding each skin layer in a target object. For example, a light beam having a short wavelength light or a light beam incident to a corresponding target object at a large incident angle may be used to acquire characteristics of a shallow skin layer, whereas a light beam having a long wavelength or a light beam incident to a corresponding target object at a small incident angle may be used to acquire characteristic of a deep skin layer. In such a case, it may not be necessary for the controller 210 to determine an optimum light.

Figure 10:
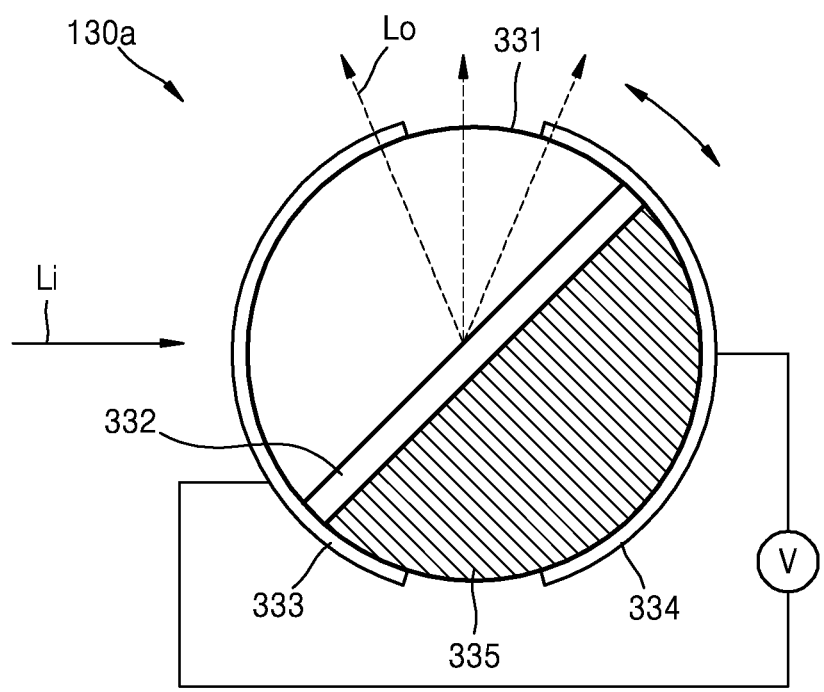
FIG. 10 is a diagram showing a light direction controller in the biological information measuring apparatus of FIG. 1, according to another exemplary embodiment.

FIG. 10 is a diagram showing a light direction controller 130a in the biological information measuring apparatus 100 of FIG. 1, according to another exemplary embodiment.

The light direction controller 130a according to another exemplary embodiment includes a film 331 that provides a spherical space, a reflective plate 332 disposed inside the film 331, and a liquid crystal material 335 disposed between a pair of electrodes 333 and 334, which surround the outer surfaces of the reflective plate 332 and the film 331, and the reflective plate 332 and the film 331, where location of the liquid crystal material 335 may be changed by a voltage between the pair of electrodes 333 and 334. The reflective plate 332 may be disposed, such that the space inside the film 331 is divided into two regions. Furthermore, the liquid crystal material 335 may be disposed in one of the two regions, whereas a material that is not mixed with the liquid crystal material 335 (e.g., the air) may be disposed in the other one of the two regions.

Location of the liquid crystal material 335 is changed based on a voltage applied to the pair of electrodes 333 and 334, and location of the reflective plate 332 may also be changed in correspondence to a change of the location of the liquid crystal material 335. Reflection of a light beam incident to the reflective plate 332 may also be adjusted according to a change of the location of the reflective plate 332. In another example, the light direction controller 130a may include a MEMS mirror that electrically controls an angle of reflection.

Figure 11:
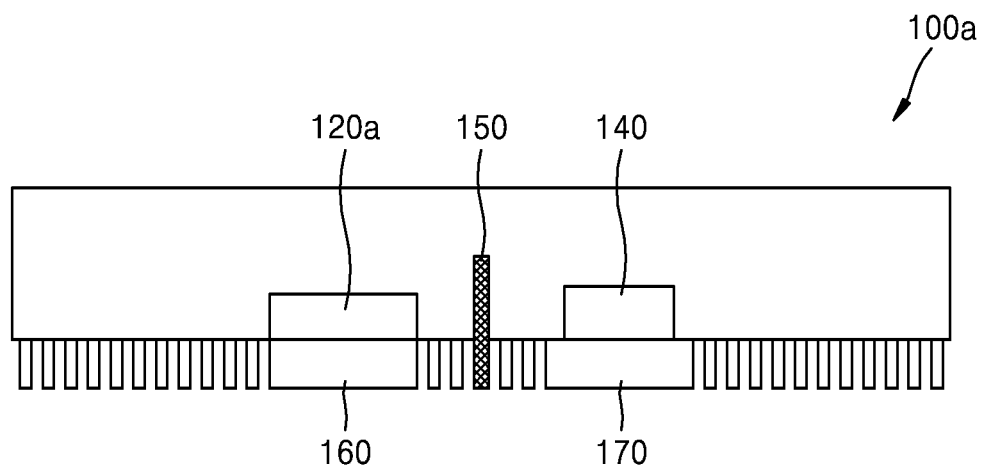
FIG. 11 is a lateral sectional diagram showing a schematic configuration of a biological information measuring according to another exemplary embodiment.
Figure 12:
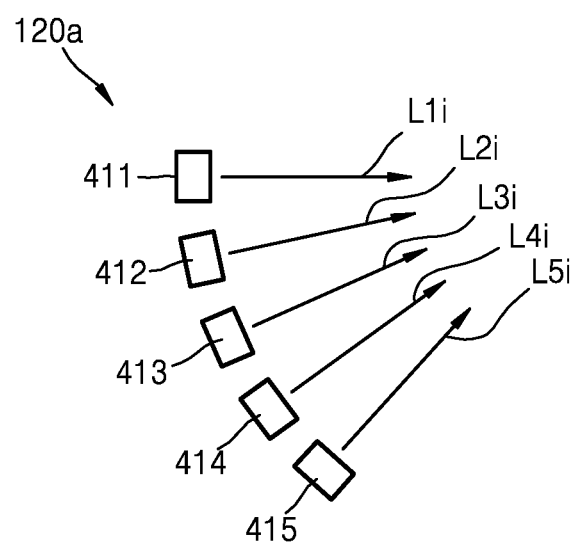
FIG. 12 is a diagram showing a schematic configuration of a light emitter of FIG. 11 according to an exemplary embodiment.

FIG. 11 is a lateral sectional diagram showing a schematic configuration of a biological information measuring apparatus 100a according to another exemplary embodiment, and FIG. 12 is a diagram showing a schematic configuration of a light emitter 110a of FIG. 11.

The light emitter 110a of the biological information measuring apparatus 100a shown in FIG. 11 may omit a light direction controller. Instead, the light emitter 110a of the biological information measuring apparatus 100a may include a plurality of light sources 411, 412, 413, 414, and 415 that emit light beams corresponding to different incident angles. Here, each of the plurality of light sources 411, 412, 413, 414, and 415 may emit a light beam having a single wavelength or the plurality of light sources 411, 412, 413, 414, and 415 may emit light beams having wavelengths different from one another. An incident angle of a light beam may be adjusted as any one of the light sources 411, 412, 413, 414, and 415 emits the light beam. In other words, an incident angle of a light beam may be adjusted in a switching manner so that at least one of the plurality of light sources 411, 412, 413, 414, and 415 emits a light beam and the other light sources emit no light beam. The light direction control shown in FIG. 11 may cause light beams emitted by the plurality of light sources 411, 412, 413, 414 and 415 to be concentrated at a particular point.

Although it is described above that the plurality of light sources 411, 412, 413, 414, and 415 of FIG. 12 emit light beams one by one in a switching manner or sequentially emit light beams one by one, the present disclosure is not limited thereto. The plurality of light sources 411, 412, 413, 414, and 415 may emit light beams simultaneously, and the light detector may also detect a plurality of light beams simultaneously.

Figure 13:
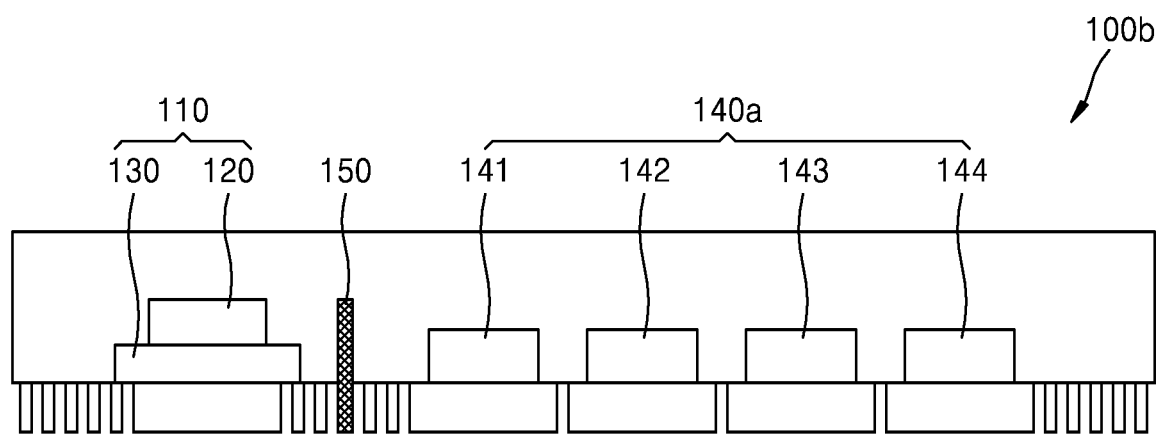
FIG. 13 is a lateral sectional diagram showing a schematic configuration of a biological information measuring apparatus according to another exemplary embodiment.
Figure 14:
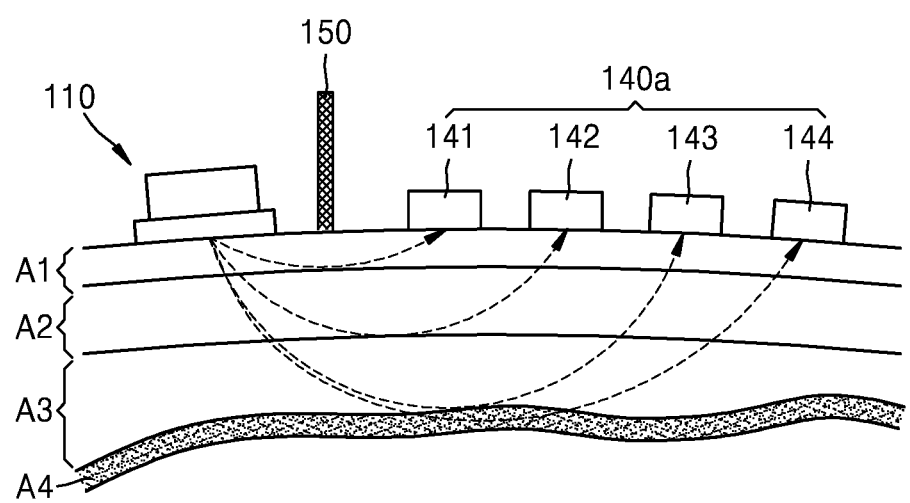
FIG. 14 is a diagram for describing an operation of the biological information measuring apparatus of FIG. 13 according to an exemplary embodiment.

FIG. 13 is a lateral sectional diagram showing a schematic configuration of a biological information measuring apparatus 100b according to another exemplary embodiment, and FIG. 14 is a diagram for describing an operation of the biological information measuring apparatus 100b of FIG. 13.

As shown in FIGS. 13 and 14, the biological information measuring apparatus 100b according to an exemplary embodiment is an attachment type and may minimize an influence due to a gap between the biological information measuring apparatus 100b and a skin. Furthermore, a light detector 140a of the biological information measuring apparatus 100b may include a plurality of sub-light detectors 141, 142, 143 and 144. As shown in FIG. 13, the plurality of sub-light detectors 141, 142, 143, and 144 may detect light beams corresponding to different trajectories, respectively. Therefore, light beams detected by the plurality of sub-light detectors 141, 142, 143, and 144 may be used to acquire biological information according to skin depths. Alternatively, at least one of light beams detected by the plurality of sub-light detectors 141, 142, 143, and 144 may be used to acquire biological information at a particularly location.

Meanwhile, the light emitter 110 may adjust incident angles of light beams incident to a target object differently by using an active type light direction controller, such that the light beams travel in trajectories different from one another. Alternatively, the light emitter 110 may use a passive-type light direction controller to adjust light beams to travel in trajectories different from one another. For example, the light emitter 110 may emit light beams having wavelengths different from one another or a plurality of light sources may sequentially or simultaneously emit light beams at incident angles different from one another. Therefore, light beams emitted from the light emitter 110 travel in the object in trajectories different from one another, and the light detector 140a may detect light beams that travel in trajectories different from one another and acquire biological information different from one another.

The processor 220 of the biological information acquiring apparatus 200 may acquire biological information regarding a first skin layer A1 using a light beam detected by a first sub-light detector 141, biological information regarding a second skin layer A2 may be acquired using a light beam detected by a second sub-light detector 142, biological information regarding a third skin layer A3 may be acquired using a light beam detected by a third sub-light detector 143, and biological information regarding a blood vessel A4 may be acquired by using a light beam detected by a fourth sub-light detector 144.

Figure 15:
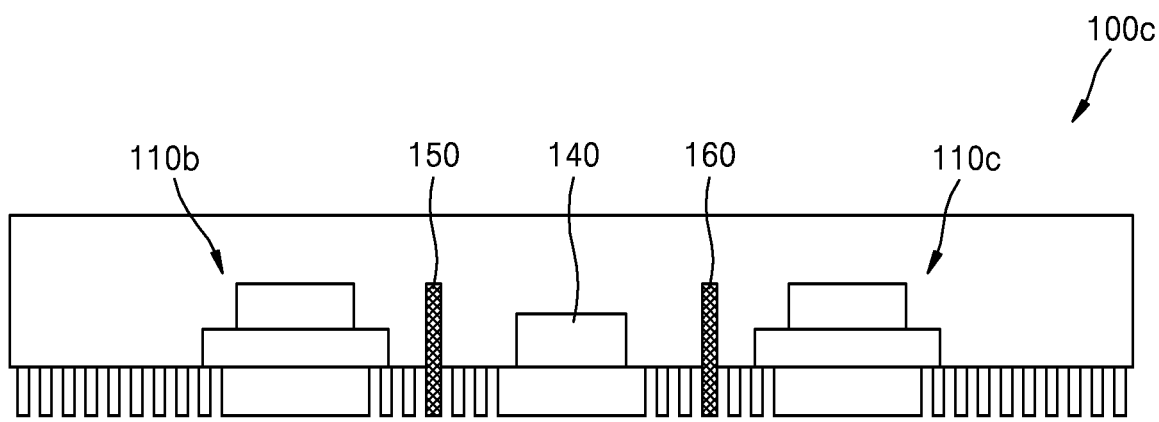
FIG. 15 is a lateral sectional diagram showing a schematic configuration of a biological information measuring apparatus according to another exemplary embodiment.
Figure 16:
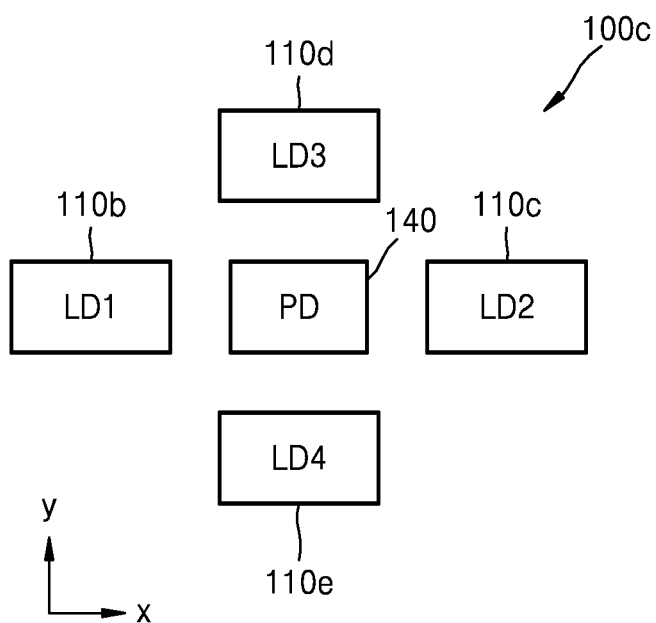
FIG. 16 is a diagram showing an arrangement of a plurality of light emitters of the biological information measuring apparatus of FIG. 15 according to an exemplary embodiment.
Figure 17:
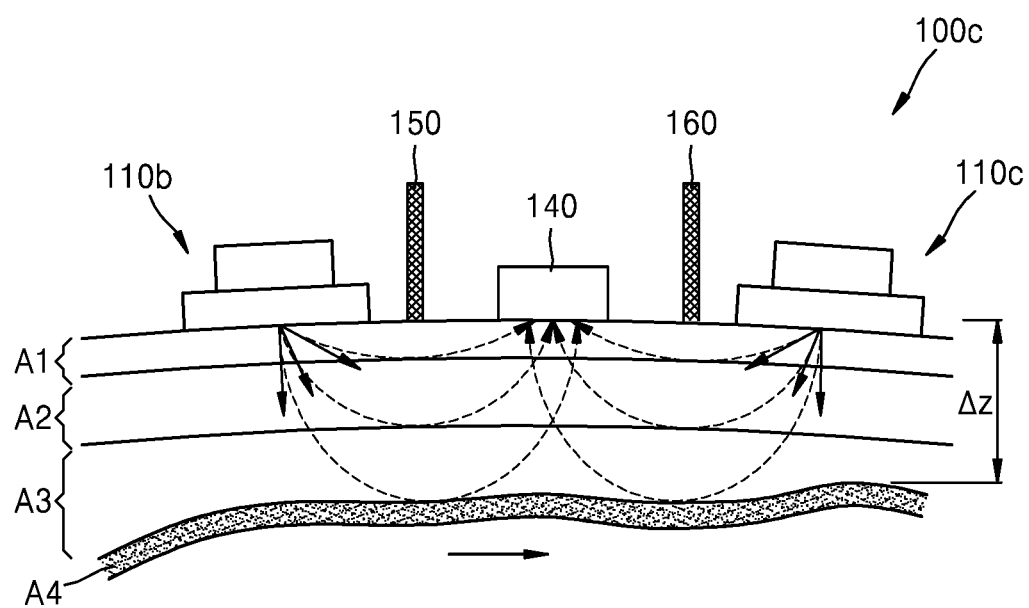
FIG. 17 is a diagram for describing an operation of the biological information measuring apparatus of FIG. 15 according to an exemplary embodiment.

FIG. 15 is a lateral sectional diagram showing a schematic configuration of a biological information measuring apparatus 100c according to another exemplary embodiment, and FIG. 16 is a diagram showing an arrangement of a plurality of light emitters 110b, 110c, 110d, and 110e of the biological information measuring apparatus 100c of FIG. 15. FIG. 17 is a diagram for describing an operation of the biological information measuring apparatus 100c of FIG. 15, and FIGS. 18 through 20 are diagrams for describing the Doppler effect observed when the biological information measuring apparatus 100 acquires biological information.

A plurality of light emitters may include at least two light emitters 110b and 110c disposed apart from each other. For example, as shown in FIG. 16, the plurality of light emitters may include at least four light emitters 110b, 110c, 110d, and 110e that are 2-dimensionally disposed around the light detector 140 and emit light beams having a single wavelength. Velocity of a blood flow may be acquired by using the Doppler effect from a light beam detected by the light detector 140 of the biological information measuring apparatus 100c. In particular, the biological information acquiring apparatus 100c in which the plurality of light emitters 110b, 110c, 110d, and 110e are 2-dimensionally disposed may detect a displacement of the blood vessel in a target object from a detected light beam and may acquire a biaxial blood flow velocity.

Figure 18:
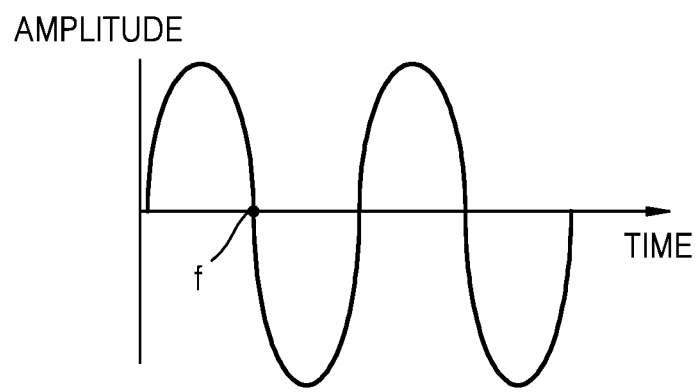
FIGS. 18 through 20 are diagrams for describing the Doppler effect observed when the biological information measuring apparatus acquires biological information according to an exemplary embodiment.
Figure 19:
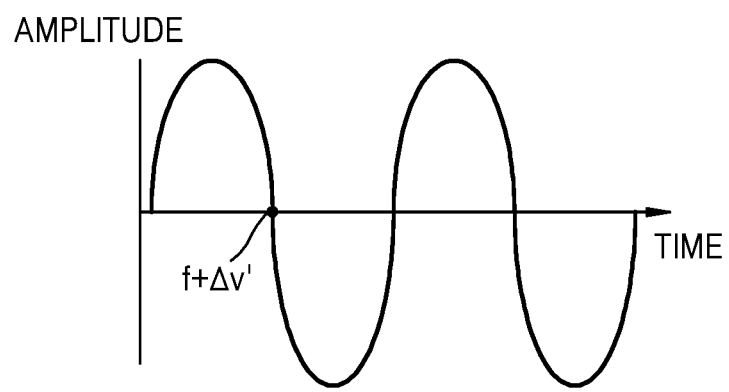
Figure 20:
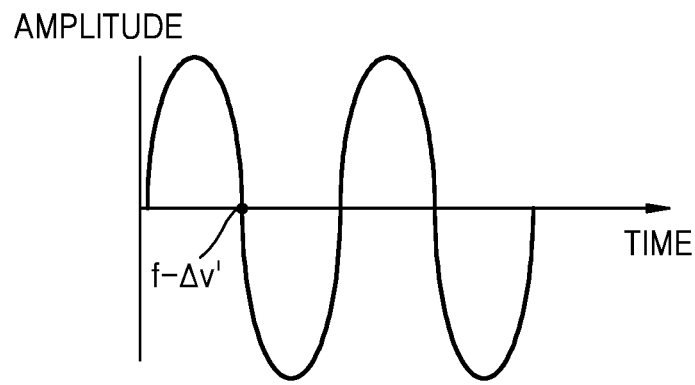

For example, when a light beam having the frequency as shown in FIG. 18 is emitted to a material of interest in a blood vessel (e.g., red blood cells), the light detector 140 may detect light beams having the frequencies as shown in FIGS. 19 and 20. The detected light beams may include a light beam having a frequency shorter than that of the emitted light beam and a light beam having a frequency longer than that of the emitted light beam. Since the material of interest in the blood vessel is moving, the frequency of a detected light beam varies according to the locations of the light emitters 110b, 110c, 110d, and 110e. The phenomenon is referred to as the Doppler effect, and the biological information acquiring apparatus 200 may acquire velocity of the material of interest, that is, velocity of a blood flow, using the Doppler effect.

Meanwhile, when thickness of a skin wall varies from one object to another, e.g., from one person to another, and when angles of incidence of light beams incident to a target object are limited, an error may occur in velocity of a blood flow. Since the biological information measuring apparatus 100 according to an exemplary embodiment is capable of adjusting an incident angle of a light beam incident to a target object, the biological information measuring apparatus 100 may determine an optimum incident angle according to a depth of a blood vessel and detect a light beam that is incident to the target object at the optimum incident angle and reacted with a material of interest. Therefore, since the Doppler flowmeter principle is applied to a detected light beam, more accurate blood flow velocity may be acquired. In other words, an angle of incidence may be adjusted without a trouble for aligning the biological information measuring apparatus 100 to a location of a blood vessel inside a skin, and the biological information acquiring apparatus 200 may acquire a velocity of a blood flow more accurately by using biaxial information. Therefore, a blood flow velocity may be acquired with minimum influence from a skin thickness, and a blood pressure may be acquired from the blood flow velocity. Furthermore, various biological information regarding the interior of the target object may also be obtained.

Figure 21:
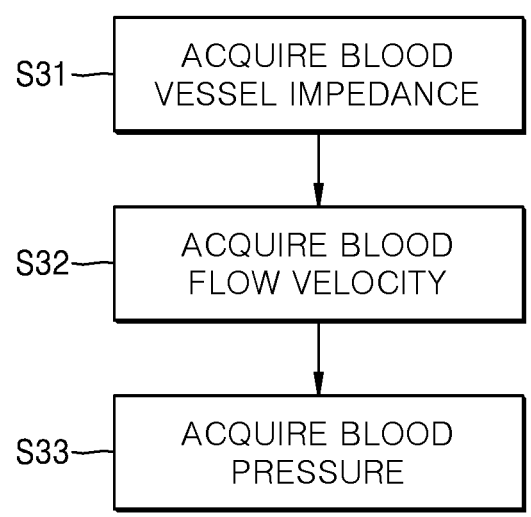
FIG. 21 is a flowchart of a method of measuring a blood pressure using the biological information measuring apparatus of FIG. 15 according to an exemplary embodiment.

FIG. 21 is a flowchart of a method of measuring a blood pressure using the biological information measuring apparatus 100C of FIG. 15. The biological information acquiring apparatus 200 may acquire blood vessel impedance, e.g., elasticity of a blood vessel, by emitting a light beam onto a blood vessel surface in operation S31. The biological information acquiring apparatus 200 may determine an optimum light beam regarding the blood vessel surface by emitting light beams to a target object according to respective incident angles or respective wavelengths and comparing detected light beams with one another. For example, in case of pulsation, an optimum light beam may be determined by using amplitudes that vary according to depths of a skin layer between a blood vessel and the biological information measuring apparatus 100c. The biological information acquiring apparatus 200 may acquire waveform information based on a movement of the blood vessel surface from the determined optimum light beam. Next, the elasticity of the blood vessel may be determined from the waveform information, and the blood vessel impedance may be estimated based on the elasticity of the blood vessel.

Furthermore, the biological information acquiring apparatus 200 may emit a light beam into a blood vessel to acquire a blood flow velocity in operation S32. Light beams emitted by two or more light emitters symmetrically arranged around the light detector 140 as described above may be used to acquire the blood flow velocity. The Doppler effect may be applied to the detected light beams to acquire the blood flow velocity.

Next, the biological information acquiring apparatus 200 may acquire a blood pressure by using the blood vessel impedance and the blood flow velocity in operation S33. A blood pressure is proportional to the product of a blood flow velocity and blood vessel impedance. As described above, when a blood pressure is measured, the blood pressure may be measured more accurately by applying the biological information measuring apparatus 100d according to an exemplary embodiment.

Figure 22:
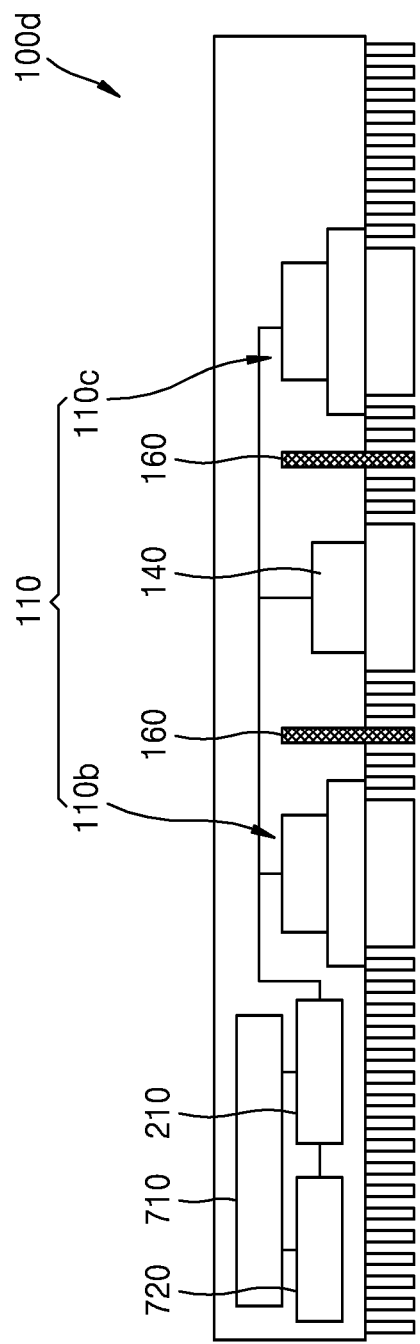
FIG. 22 is a lateral sectional diagram showing a schematic configuration of a biological information measuring apparatus according to another exemplary embodiment.

FIG. 22 is a lateral sectional diagram showing a schematic configuration of a biological information measuring apparatus 100d according to another exemplary embodiment.

The biological information measuring apparatus 100d may include the light emitter 110, the light detector 140, and the controller 210. The biological information measuring apparatus 100 further includes a communication interface 710 that wirelessly communicates with the outside, and a battery 720 that supplies power. The biological information measuring apparatus 100d of FIG. 22 may transmit a detected light beam or an optimum light beam to an external device via the communication interface 710. The external device includes the processor 200, thus being capable of acquiring biological information by using the detected light beam or the optimum light beam.

Since a common attachment band-type system uses an adhesive band, it is difficult to re-use the common attachment band-type system. However, the biological information measuring apparatus 100d according to an exemplary embodiment may be re-used a multiple number of times, because protrusion-type nano structure columns are disposed on a surface of the biological information measuring apparatus 100d and may be attached to and detached from a skin of a target object. A housing of the biological information measuring apparatus 100d may include an overall flexible material. It may be difficult for such the flexible biological information measuring apparatus 100d to measure biological information than a hard-type biological information measuring apparatus. Since an angle of incidence of a light beam may be adaptively changed according to a material of interest, a light beam may be detected at the maximum sensitivity by adjusting the trajectory.

Figure 23:
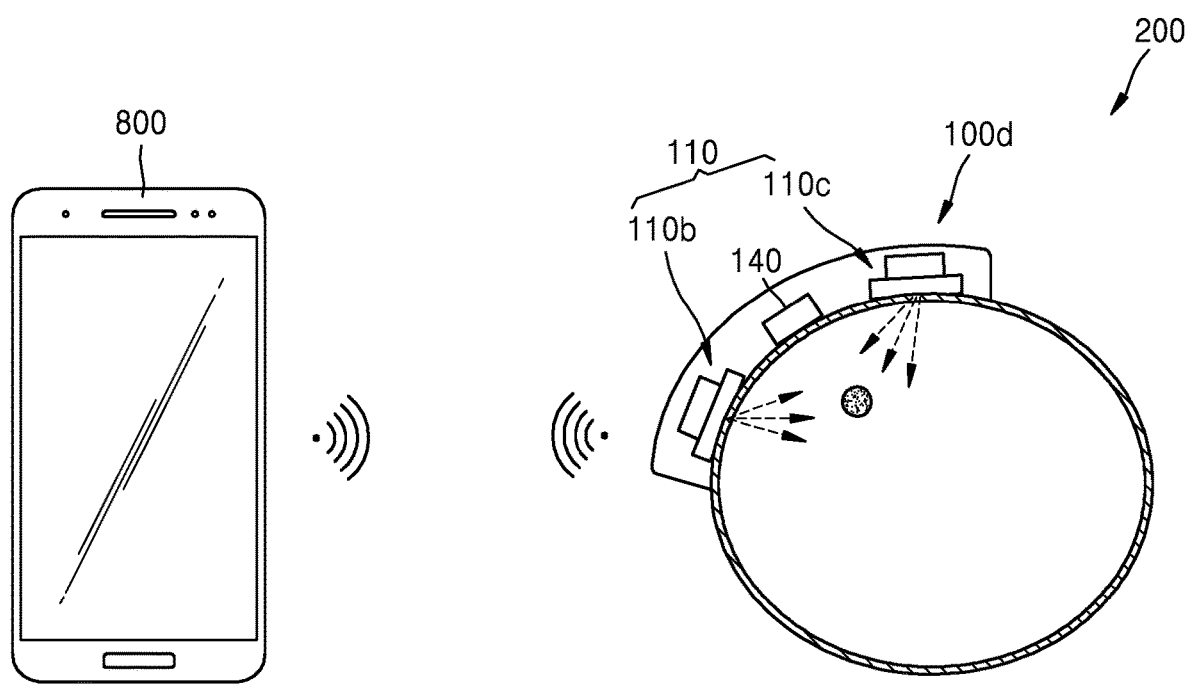
FIG. 23 is a diagram showing a schematic configuration of a biological information acquiring system according to another exemplary embodiment.

FIG. 23 is a diagram showing a schematic configuration of a biological information acquiring system according to another exemplary embodiment.

The biological information measuring apparatus 100d according to an exemplary embodiment may be a band-type that may be attached to a skin. As shown in FIG. 23, the biological information measuring apparatus 100d with an attachment structure may be disposed on a skin. Since the biological information measuring apparatus 100d may adjust bias of a light beam, the biological information measuring apparatus 100d may acquire pulse pressure information regarding a blood vessel inside a body at the maximum sensitivity. Furthermore, the biological information measuring apparatus 100d may also include a communication interface for wirelessly communicating with an external device and a battery that may be charged wirelessly. The light emitter may emit a light beam to the target object at a deflected angle. Since thickness of a skin varies from one person to another, an angle of a light beam may be deflected to maximize reflectivity with respect to an internal material of interest, e.g., blood vessels, in order to eliminate factors based on the thickness of the skin as much as possible. A lens structure for condensing a light beam may be further disposed in front of the light detector 140, where the lens structure may be useful for acquiring a light beam at a high sensitivity.

The biological information measuring apparatus 100d may wirelessly communicate with an external device 800, such as a mobile device, to acquire control and data from the external device 800. Furthermore, the biological information measuring apparatus 100d may be wirelessly charged by the external device 800 and, after the band-type biological information measuring apparatus 100d is attached to a body, the external device 800 may charge the band-type biological information measuring apparatus 100d wirelessly and monitor biological information continuously for 24 hours. Furthermore, the external device 800 may acquire biological information based on optical information received from the biological information measuring apparatus 100d. In other words, the external device 800 may be a biological information acquiring apparatus.

According to a biological information measuring apparatus, a method of acquiring biological information, and a biological information acquiring apparatus according to the exemplary embodiments, an optical path (that is, a trajectory in a target object) may be adjusted by adjusting a direction of a light beam. Therefore, an error due to a skin may be reduced and biological information regarding the interior of skin may be accurately acquired.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A biological information measuring apparatus comprising:
   a light emitter comprising:
      a light source configured to emit a plurality of light beams to a target object;
      a light direction controller comprising:
         a film that provides a spherical space;
         a first electrode and a second electrode that surround an outer surface of the film;
         a reflective plate that is disposed on the film to divide the spherical space of the film into a first region and a second region, and that changes output angles of the plurality of light beams according to a voltage applied between the first electrode and the second electrode; and
         a liquid crystal material that is disposed in either the first region or the second region of the film, between the first electrode and the second electrode,
   a light detector configured to detect the plurality of light beams returning from the target object along trajectories different from one another and acquire biological information of the target object based on at least one of the detected plurality of light beams,
   wherein a location of the liquid crystal material in the light direction controller is changed according to the voltage applied between the first electrode and the second electrode of the light direction controller.

2. The biological information measuring apparatus of claim 1, wherein the liquid crystal material is disposed in the first region of the film, and a material that is not mixed with the liquid crystal material is disposed in the second region of the film.

3. The biological information measuring apparatus of claim 1, wherein the plurality of light beams are emitted in directions different from one another.

4. The biological information measuring apparatus of claim 3, wherein the plurality of light beams have a single wavelength or wavelengths different from one another.

5. The biological information measuring apparatus of claim 1, wherein the plurality of light beams have multiple wavelengths,
   the biological information measuring apparatus further comprises a wavelength separating element configured to separate the plurality of light beams according to the multiple wavelengths, and
   the wavelength separating element comprises at least one of a diffraction grating and a prism.

6. The biological information measuring apparatus of claim 1, wherein the light source is a first light source, and the light emitter comprises at least two light sources comprising the first light source and a second light source,
   wherein the light detector is disposed between the at least two light sources,
   wherein a wavelength of first light beams emitted from the first light source is different from a wavelength of second light beams emitted from the second light source.

7. The biological information measuring apparatus of claim 1, wherein the light emitter comprises at least four light sources which are two-dimensionally arranged around the light detector and configured to emit the plurality of light beams having a single wavelength, and
   wherein the light source is one of the at least four light sources.

8. The biological information measuring apparatus of claim 1, wherein a meta-material is disposed between the light source and an outer surface of the biological information measuring apparatus to adjust the output angles of the plurality of light beams that are output from the outer surface of the biological information measuring apparatus.

9. The biological information measuring apparatus of claim 1, wherein a partitioning wall is disposed between the light emitter and the light detector.

10. A method of acquiring biological information, the method comprising:
    emitting, by a light source, a plurality of light beams to a target object through a light direction controller comprising:
       a film that provides a spherical space;
       a first electrode and a second electrode that surround an outer surface of the film;
       a reflective plate that is disposed on the film to divide the spherical space of the film into a first region and a second region, and that changes output angles of the plurality of light beams according to a voltage applied between the first electrode and the second electrode; and
       a liquid crystal material that is disposed in either the first region or the second region of the film, between the first electrode and the second electrode;
    detecting the plurality of light beams returning from the target object along trajectories different from one another; and
    acquiring biological information of the target object based on at least one of the detected plurality of light beams,
    wherein a location of the liquid crystal material in the light direction controller is changed according to the voltage applied between the first electrode and the second electrode of the light direction controller.

11. The method of claim 10, wherein the acquiring the biological information comprises:
    determining a light beam of the plurality of light beams as an optimum light beam in response to a correlation between the light beam and a reference light beam being greater than or equal to a predetermined value; and
    acquiring the biological information from the optimum light beam.

12. The method of claim 10, wherein the emitting the plurality of light beams comprises emitting at least two light beams along intersecting trajectories.

13. The method of claim 12, further comprising acquiring a blood flow velocity of the target object based on the at least one of the detected plurality of light beams by using a Doppler effect.

14. A biological information measuring band comprising the biological information measuring apparatus of claim 1 and configured to measure the biological information when the biological information measuring band is in contact with a skin of the target object.

15. The biological information measuring band of claim 14, further comprising an attachment layer disposed on a skin contacting surface of the biological information measuring apparatus, the attachment layer comprising a protruding microstructure that is attachable to and detachable from the skin.

16. The biological information measuring band of claim 15, further comprising:
- a wireless communication interface configured to wirelessly communicate with an external device;
- a controller configured to control the light emitter, the light detector, and the wireless communication interface; and
- a battery configured to supply power.

17. The biological information measuring band of claim 14, wherein the biological information measuring apparatus is bendable.

* * * * *